US 6,503,209 B2

(12) United States Patent
Hakky et al.

(10) Patent No.: US 6,503,209 B2
(45) Date of Patent: Jan. 7, 2003

(54) NON-INVASIVE FOCUSED ENERGY BLOOD WITHDRAWAL AND ANALYSIS SYSTEM

(76) Inventors: Said I. Hakky, 8547 Merrimoor Blvd. E., Largo, FL (US) 33777-3145; A-Hamid Hakki, 1508 Sturbridge Ct., Dunedin, FL (US) 34698

( * ) Notice: Subject to any disclaimer, the term of this patent is extended or adjusted under 35 U.S.C. 154(b) by 53 days.

(21) Appl. No.: 09/859,592

(22) Filed: May 18, 2001

(65) Prior Publication Data

US 2002/0173732 A1 Nov. 21, 2002

(51) Int. Cl.$^7$ ............................................... A61B 5/00
(52) U.S. Cl. ....................... 600/573; 600/576; 600/578; 606/13; 606/9
(58) Field of Search ................................ 600/573–578; 606/2, 9, 10, 13, 16

(56) References Cited

U.S. PATENT DOCUMENTS

| | | | |
|---|---|---|---|
| 5,131,403 A | | 7/1992 | Haynes ........................ 600/573 |
| 5,165,418 A | * | 11/1992 | Tankovich ................... 600/573 |
| 5,554,153 A | * | 9/1996 | Costello et al. ................ 606/11 |
| 5,617,851 A | | 4/1997 | Lipkovker ................... 600/573 |
| 5,636,632 A | | 6/1997 | Bommannan et al. ....... 600/576 |
| 5,735,273 A | | 4/1998 | Kurnik et al. ............... 600/345 |
| 5,771,890 A | | 6/1998 | Tamada ....................... 600/347 |
| 5,827,183 A | | 10/1998 | Kurnik et al. ............... 600/345 |
| 5,895,362 A | | 4/1999 | Elstrom et al. .............. 600/573 |
| 5,925,036 A | * | 7/1999 | Maxwell, III ................. 606/13 |
| 5,947,957 A | * | 9/1999 | Morris ......................... 600/573 |
| 5,954,685 A | | 9/1999 | Tierney ......................... 604/20 |
| 5,989,409 A | | 11/1999 | Kurnik et al. ............... 205/792 |
| 6,023,629 A | | 2/2000 | Tamada ....................... 600/347 |
| 6,027,459 A | * | 2/2000 | Shain et al. .................. 600/573 |
| 6,041,253 A | | 3/2000 | Kost et al. ..................... 604/20 |
| 6,059,776 A | * | 5/2000 | Gatto ............................ 606/13 |
| 6,093,156 A | * | 7/2000 | Cunningham et al. ....... 600/573 |
| 6,306,104 B1 | * | 10/2001 | Cunningham et al. ....... 600/573 |

OTHER PUBLICATIONS

"Erbium Laser Skin Smoothing", advertisement at web address http://www.peppercorn.md.com, Mar. 29, 2001.
P.S. Hersh, et al., "Excimer Laser Photorefractive Keratectomy", *Opthalmic Practice*, vol. 13, 1995, pp. 126–133.
Vitros Products, Product Information Sheet, GLU slides, Nov. 1996, p. 1.
Vitros Products, Product Information Sheet, TP slides, Nov. 1996, pp. 1 and 7.
Vitros Products, Product Information Sheet, BUN/UREA slides, Nov. 1996, p. 1.
Vitros Products, Product Information Sheet, Ca slides, Nov. 1996, p. 1.
Vitros Products, Product Information Sheet, Na slides, Nov. 1996, p. 1.
Vitros Products, Product Information Sheet, Cl slides, Nov. 1996, p. 1.
Vitros Products, Product Information Sheet, ECO$_2$ slides, Nov. 1996, p. 1.

* cited by examiner

*Primary Examiner*—Patrick Brinson
(74) *Attorney, Agent, or Firm*—Rosenberg, Klein & Lee

(57) ABSTRACT

A non-invasive focused energy blood withdrawal and analysis system (1) is provided. A laser energy source (11) and a vacuum pump (9) are mounted within a portable housing. A focused laser beam is directed on an epidermal layer to create a microscopic incision in the epidermis of a patient. Vacuum pump (9) draws a blood sample from the microscopic incision through a disposable fluid displacement device (2). A removable dry slide is placed in the fluid path of the blood sample to receive the blood sample. Further, sensor elements (6 and 7) are mounted within the portable housing on either side of the removable dry slide (8) to perform blood analysis. A logic processing unit (5) is provided in electrical communication with sensor elements (6 and 7) for performing the necessary blood analysis.

20 Claims, 9 Drawing Sheets

NON-INVASIVE FOCUSED ENERGY BLOOD WITHDRAWAL AND ANALYSIS SYSTEM

BACKGROUND OF THE INVENTION

1. Field of the Invention

The subject invention relates to a focused energy blood withdrawal and analysis system.

Further, the subject invention relates to a non-invasive focused energy blood withdrawal and analysis system which permits microscopic openings or holes to be formed into the epidermal layer of a patient in a substantially rapid manner with a minimization of dermal nerve stimulation.

Still further, the subject invention directs itself to a blood withdrawal and analysis system wherein the major components are located within a hand-held portable housing and transmit parameters being measured to an external display.

The subject invention relates to a non-invasive focused energy blood withdrawal and analysis system. In particular, the present invention directs itself to a hand-held, portable system for creating microscopic incisions in an epidermal layer. More particularly, this invention is directed towards a system for drawing blood from the incision and analyzing the drawn blood sample for various blood components. More particularly, this invention directs itself to a blood withdrawal system using a focused energy beam to incise the epidermal layer.

Further, the hand-held system has a vacuum pump mounted within the portable housing in order to draw a blood sample from the incision in the epidermal layer. Additionally, this invention directs itself to a blood analysis system having sensor elements mounted within the housing for substantially instantaneous analysis of the blood sample.

Still further, this invention is directed to a non-invasive focused energy blood withdrawal and analysis system which includes an energy source located within the housing for generating an energy beam with the energy beam being focused on an epidermal layer to create a microscopic opening in the epidermal layer.

Still further, the subject invention relates to a non-invasive focused energy blood withdrawal and analysis system which includes a logic processing unit coupled to an energy source, all of which are mounted within a housing.

Additionally, the subject invention relates to a non-invasive focused energy blood withdrawal and analysis system which combines a vacuum pump, a logic processing unit, and an energy source within a housing which is portable in nature and adapted to be hand-held.

Further, the subject invention pertains to a non-invasive focused energy blood withdrawal and analysis system which includes an energy source, a vacuum pump, and a slide located in the fluid path of a blood sample withdrawn from an epidermal layer upon actuation of the energy source under control of the logic processing unit.

Additionally, the subject invention relates to a non-invasive focused energy blood withdrawal and analysis system which includes a display for displaying parameters of blood withdrawn through the epidermal layer where the display is coupled to a logic processing unit and a power source.

More in particular, this invention is directed to a non-invasive focused energy blood withdrawal and analysis system where a slide for collecting blood being drawn from an epidermal layer is removably mounted within a housing and is placed in the fluid path of the blood sample being drawn by a vacuum pump mounted within the housing.

Still further, the subject invention relates to a non-invasive focused energy blood withdrawal and analysis system which provides for a pulsed energy wave, delivered in a repeated programmed manner, in order to precisely control the diameter of an opening or hole to be made in the skin and further to control the depth of the hole being generated.

Further this invention provides for a non-invasive focused energy blood withdrawal and analysis system where focused energy in the form of a laser, a sonic beam or an electrical current is used to incise an epidermal layer whereby the focused layer transmission components are located in a portable housing.

2. Prior Art

Blood withdrawal and analysis systems are known in the art. In general, such prior art systems include some type of focused energy for incising the epidermal layer. In many instances, however, the blood to be analyzed flows through the incision of the epidermal layer under the body's own blood pressure which is a slow and inefficient process. Further, prior art analysis systems often draw the blood sample within permanent analysis chamber. Not only is the preparation of a special chamber time consuming and generally inefficient, but it is also relatively unsanitary. It is a purpose of the subject invention to provide a combination of elements making up a hand-held, portable blood withdrawal and analysis system which allows for the use of both a focused energy beam to incise an epidermal layer, and an adjustable vacuum pump for applying variable suction to the incision on the epidermis. Further, the subject invention provides a removable dry slide positioned in the flow of the blood sample for collecting the blood sample for analysis. The removable slide is replaceable within the housing subsequent to a particular test being completed.

One such prior art withdrawal and analysis system is shown in U.S. Pat. No. 5,617,851. This reference is directed to an ultrasonic transdermal system for withdrawing fluid from an organism and determining the concentration of a substance in the fluid. This system includes an ultrasonic transducer for generating pulses to be focused onto the skin of an organism. The trauma of the ultrasonic pulse causes the dermal-epidermal junction membrane and the capillary endothelial joints to open, allowing blood to be drawn. Substances to be detected in the blood are sensed by a substance sensing transducer, the output of the transducer being analyzed by a test data processor. This system does not include an additional vacuum pump for drawing the blood from the incision made in the skin.

Another such prior art blood withdrawal system is shown in U.S. Pat. No. 5,131,403. This reference is directed to a method for obtaining blood using iontrophoresis. This system uses electric current to penetrate the epidermal layer of a patient. The system, however, does not include an adjustable vacuum for aiding in the drawing of blood through the microscopic puncture in the skin.

U.S. Pat. No. 5,989,409 shows a prior art system directed to a method for glucose sensing. This system includes a plurality of electrodes for generating an electrical current to be sent through the skin of a patient, thereby drawing molecules, including glucose, through the patient's skin and into a hydrogel patch. This reference does not include sensor elements allowing for the sensing of a variety of chemical compounds in blood, nor does it include a vacuum pump for expeditiously drawing blood through the skin.

U.S. Pat. No. 5,954,685 shows a prior art system directed to an electrochemical sensor with a dual purpose electrode.

This system utilizes a pair of electrodes to generate an electrical current in a subject's skin. Blood is thus drawn through the skin and collected for analysis in a reservoir system. The system, however, does not include a vacuum pump for aiding in the drawing of the blood through the skin.

Another prior art blood withdrawal system is shown in U.S. Pat. No. 5,895,362. This reference is directed to transdermal transport using ultrasonic standing waves. The system utilizes a sonic generator for generating an ultrasonic standing wave of a given frequency and distributing the wave over the surface of the skin. The system does not use a focused energy beam for incising of the skin, nor does it include a vacuum pump for aiding in the drawing of the blood from the epidermal layer.

None of the prior art provides for a combination of elements forming a blood analysis and withdrawal system which is hand-held, portable, includes a focused energy beam for creating a microscopic incision in the epidermal layer coupled with a vacuum pump for aiding in the drawing of the blood to be analyzed through the incision. Additionally, none of the prior art Patents provide for a removable slide to be positioned in the path of the blood sample flow within the analysis device, thus allowing for removable, sanitary analysis of the blood.

In prior art technology, various parameters have been analyzed by numerous techniques. In particular, in order to measure blood glucose, prior art techniques form an approximately 1 cm opening in the stratum corneum using perhaps some energy source such as lasers, ultrasound, or electrical current. Diffusion allows the fluid, with hydrostatic pressures approximating 0–2.0 mm Hg, to come to the surface of the skin. The amount of interstitial fluid for extraction is generally sparse in the epidermis in comparison to the dermo/epidermal layer.

In some prior art systems, suction has been used to expedite the extraction of fluid from the interstitial layers of the epidermis. However, disadvantageously, the high pressure created by the suction has been found to be painful and has led to bruising which is generally aesthetically unacceptable.

In particular, such prior art systems have disadvantageous effects, especially in the case of diabetic patients who have many tests taken over short time intervals. Numerous areas of bruising have been known to occur over the body.

Additionally, other prior art systems disclose the extracting of interstitial fluid from the superficial layers of the epidermis where the interstitial fluid is sparse. Due to the low hydrostatic pressure and the thinly dispersed interstitial fluid, the process is relatively slow. In such prior art techniques, it may take between 10 and 20 minutes to extract a single drop of the interstitial fluid. Such delays in time to measure blood glucose generally makes such a prior technique unattractive since insulin acts within 5 minutes and peaks in 20 minutes. Thus, glucose measurement in particular should be completed within 1–2 minutes and will result in a more efficient control of blood sugar to avert complications seen in diabetic patients.

SUMMARY OF THE INVENTION

The present invention provides for a non-invasive blood withdrawal and analysis system. The blood withdrawal and analysis system includes an energy source for creating a focused energy beam and a vacuum pump, both mounted within a portable hand-held housing. The system is placed against a patient's epidermal layer and the focused energy beam is used to create a microscopic incision in the epidermis. The vacuum pump aids in drawing blood from the incision through a disposable suction tube. A removable dry slide is positioned in the path of the blood sample drawn from the incision in the epidermis. Sensor elements are mounted on either side of the dry slide, within the housing, for instantaneous analysis of the blood sample. Both the disposable suction tube and the dry slide may be removed and replaced for sanitary reasons.

It is a principal objective of the subject non-invasive blood analysis and withdrawal system to provide a portable, hand-held system for the withdrawal and analysis of a blood sample.

It is a further objective of the subject blood analysis and withdrawal system to provide a focused energy beam for creating a microscopic incision in an epidermal layer.

It is a further objective of the subject invention to provide an adjustable vacuum pump for aiding in drawing of blood through the microscopic incision formed in the epidermal layer.

It is a further objective of the subject invention concept to provide a blood analysis and withdrawal system having a removable dry slide placed in the path of the blood sample flow for collecting the blood sample to be analyzed.

It is a further objective of the subject invention to provide for sensor elements mounted on either side of the dry slide for instantaneous analysis of the blood sample.

It is an important objective of the present invention to provide a blood analysis and withdrawal system having a disposable suction tube for drawing blood through a microscopic incision in the epidermis combined with a removable dry slide positioned in the flow of the blood sample, both the disposable suction tube and the dry slide being removable and replaceable for sanitary reasons.

DESCRIPTION OF THE PREFERRED EMBODIMENTS

Figure 1:
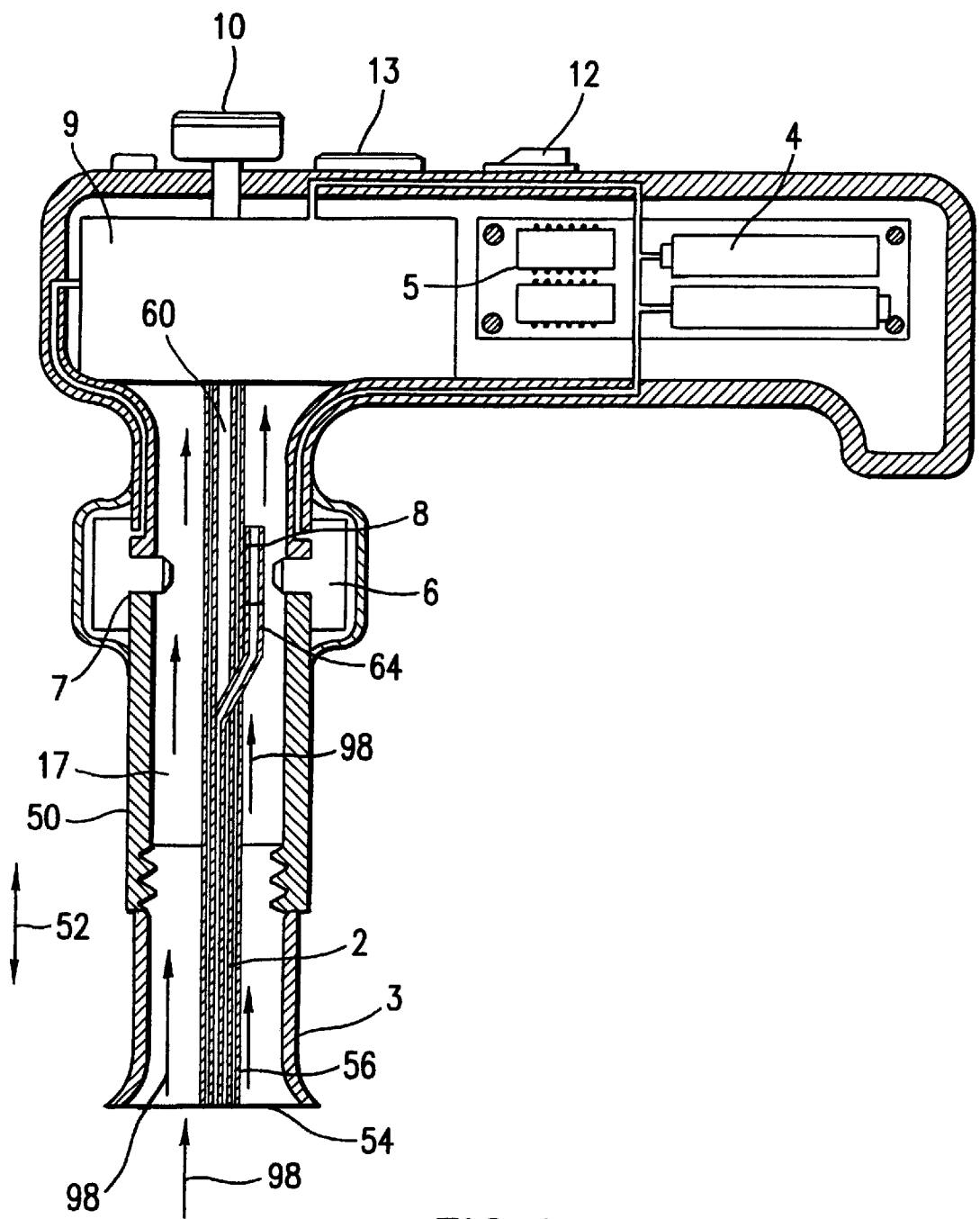
FIG. 1 is a side cut-away view of the subject non-invasive focused energy blood withdrawal and analysis system.
Figure 2:
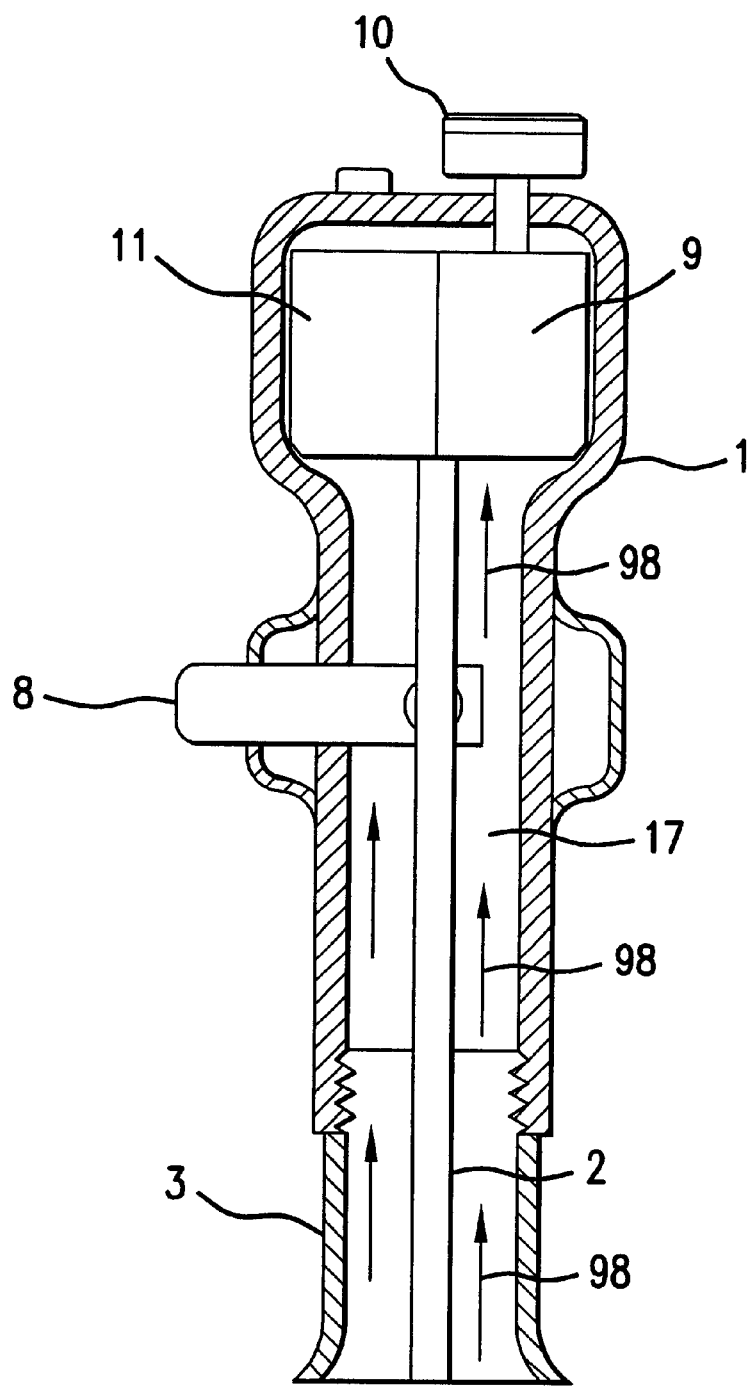
FIG. 2 is a front cut-away view of the subject non-invasive focused energy blood withdrawal and analysis system.

Referring now to FIGS. 1 and 2, there is shown a non-invasive focused energy blood withdrawal and analysis system 1. The system 1 includes a disposable fluid displacement device 2 mounted within a portable housing 50. Fixed to the base of the portable housing is a sealing member 3 which contacts a patient's epidermis which is removably fixed to housing 50 by threaded securement or some like technique such as through a friction fit. Sealing member 3 includes a flared end section which provides a stable structure for contiguous mounting to the patient's epidermis.

Non-invasive focused energy blood withdrawal and analysis system 1 is placed contiguous to the patient's epidermis. As is well-known, the skin of a patient forms an effective barrier against microbial invasion. Additionally, the skin is well-known to protect against mechanical, chemical, thermal, and photic damage. The skin is an important primary site of immuno-surveillance to block the entry of antigens and is useful in the initiation of primary immunoresponses.

The skin is composed of two layers, namely the vascular epidermis and the vascular dermis. In overall thickness, the epidermis has an average thickness of 100 micrometers. The overall epidermis consists of the stratum corneum, the stratum granulosum, the stratum spinosum, and the stratum basal. There are no blood vessels and nerves in the epidermis and thus, the amount of interstitial fluid is sparse. Blood vessels are generally located at the dermo/epidermal layer which is below the stratum basal of the epidermis and the blood vessels form plexuses of arteries and veins.

As shown in FIG. 1, the system 1 includes a vacuum pump 9 mounted within the housing 50. The vacuum pump 9 is in fluid communication with the disposable fluid displacement device 2 which is used to transport a blood sample from the patient's epidermis to a dry slide 8. As indicated by directional arrows 98 in FIGS. 1 and 2, the vacuum pump 9 creates a fluid path traveling upwards from sealing member 3 (contiguous the patient's epidermis) to the vacuum pump 9. A region of negative fluid pressure is created within the disposable fluid displacement device 2, thus allowing bodily fluids, such as blood, to be drawn up through the disposable fluid displacement device 2. The vacuum pump 9 creates a region of pressure between 2 mm Hg and 120 mm Hg. The power output of vacuum pump 9 may be variable and controllable by the user as a function of a particular procedure.

Portable, manually controllable vacuum pump systems are well-known in the art. One such vacuum pump used for medical purposes is the SonoPrep™ Skin Permeation System, produced by Sontra Medical, Inc. of Cambridge, Mass.

Referring to FIG. 1, it is seen that disposable fluid displacement device 2 extends throughout housing portion 50 in a vertical direction 52 and is in fluid communication with vacuum pump 9. Fluid displacement device 2 extends to end 54 of sealing member 3 for placement contiguous the epidermal layer of the patient. Fluid displacement device 2 may be formed of a plurality of concentric cylindrical members including an outer cylindrical section 56 and a mid-cylindrical element 58, more clearly seen in FIG. 6. Within the annulus formed by the elements 58 and 56, a path is provided in vertical direction 52 for laser energy to pass therethrough.

Central extending element 60 passing in vertical direction 52, in combination with extending element 58 forms an annulus 62 through which power lines may extend.

The elements forming fluid displacement device 2 may be composed of glass, plastic or of a metallic composition not important to the invention as herein described with the exception that the composition be suitable to accept the structural loads imposed thereon and inert with respect to chemical reactions of fluid passing therethrough.

Dry slide 8 is removably insertable within slide tubular member 64 wherein fluid is passed in substantially vertical direction 52 within fluid conduit 66 for impingement with dry slide 8 during operation of the overall system 1.

As can be seen, slide tubular member 64 provides for a non-linear fluid path within conduit 66 to allow dry slide 8 to be mounted within section 68 adjacent the annular cylinders as previously described.

In this manner, dry slide 8 may be inserted within conduit 66 and removed therefrom in a substantially simple manner. Still further, fluid being drawn in vertical direction 52 through disposable fluid displacement device to lower section 70 is angularly moved through conduit portion 72 into fluid conduit 66 in a smooth continuous non-tortuous manner.

Upon actuation of the energy beam, fluid is drawn by vacuum pump 9 through conduit section 70 in vertical direction 52 and is then smoothly moved to an external side of outer cylinder element 56.

After a sample has been collected on dry slide 8, the entire disposable fluid displacement device 2 may be removed from housing section 50 by removing device 2 from a friction fit coupling or other removable securing mechanisms, with vacuum pump 9. Once disposable device 2 has been removed from the overall housing, dry slide 8 may be slid out from or otherwise removed from section element 64.

Figure 6:
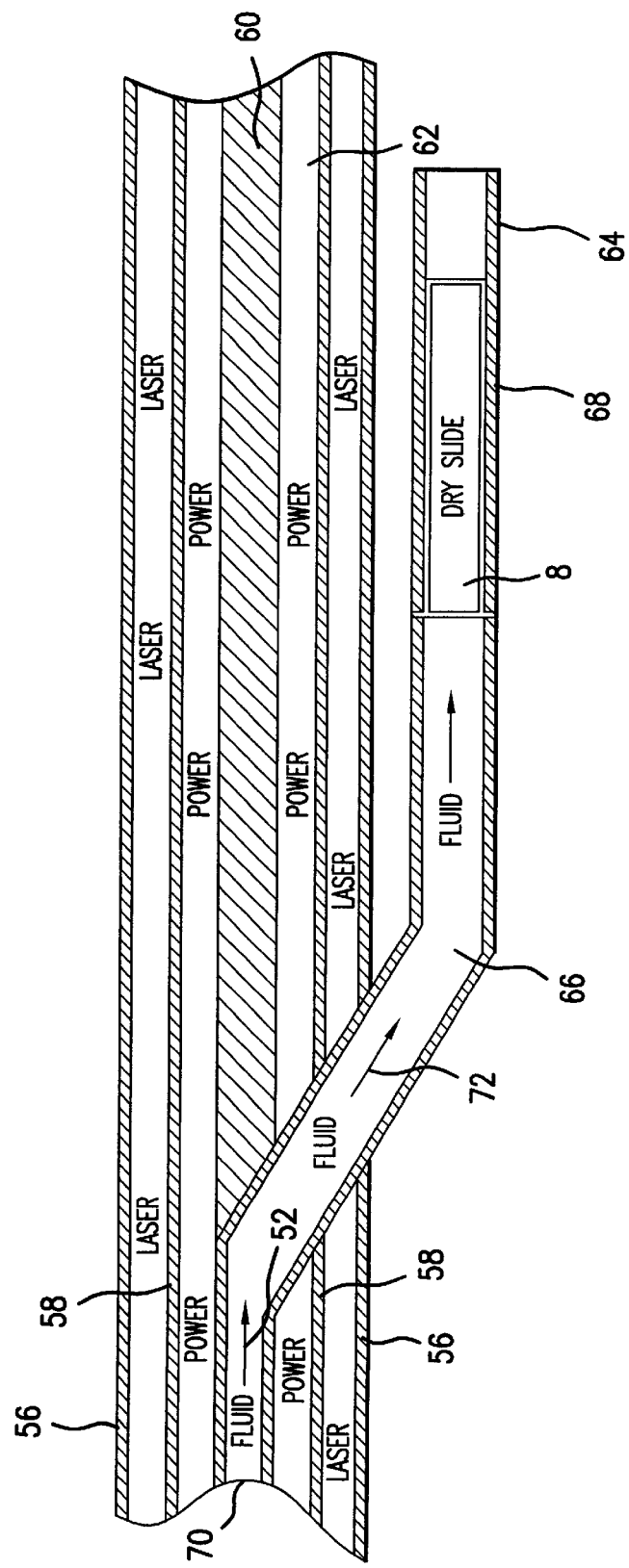
FIG. 6 is a partial cut-away side view of the non-invasive laser focused energy blood withdrawal and analysis system.

As best shown in FIGS. 1 and 6, a dry slide 8 is removably mounted within the disposable fluid device 2. Particularly, dry slide 8 is removably seated in the fluid path of the drawn blood sample, within disposable fluid displacement device 2, created by vacuum pump 9. Thus, when the system 1 is placed in contact with an epidermal layer, and sealing member 3 makes air-tight contact with the epidermal layer, bodily fluids will be drawn up through the disposable fluid displacement device 2 to be received on dry slide 8.

Dry slide 8 may be a dry, multi-layered, analytical element coated on a polyester support. Dry slide 8 generally contains a reagent layer needed for the specific test for the patient. Analytical slides for blood component analysis are well-known in the art. One such slide is the Vitros GLU™ slide manufactured by Johnson & Johnson.

Dry slide 8, disposable fluid displacement device 2, and sealing member 3 are all removable, disposable, and replaceable. After each blood sample is drawn and analyzed, dry slide 8, disposable fluid displacement device 2, and sealing member 3 are replaced in order that the system may be safely and sanitarily used on another patient.

As shown in FIG. 1 of the Drawings, sealing member 3 is removable from main body housing 50. In FIG. 1, sealing member 3 is shown as being in threaded engagement with the bottom portion of main housing 50, however, sealing member 3 may be joined to housing 50 through a friction fit engagement, or through any other suitable means.

As shown in FIG. 1, sensor elements 6 and 7 are mounted within the portable housing on either side of the removable dry slide 8. Sensors 6 and 7 may be spectrometers, colorimeters, temperature sensors, or any other type of sensor used in the analysis of bodily fluids, particularly blood. Further, sensor elements 6 and 7 may be replaceable so that the non-invasive blood analysis and withdrawal system 1 may be used for the analysis of many different types of compositions and bodily fluids. Additionally, sensor elements 6 and 7 may be cooperating elements, for example, sensor 6 may be a photodetector or spectrometer and sensor element 7 may be a light source.

The blood sample is analyzed for a variety of different components. The dry slide 8 may have a reagent layer formed thereon to aid in the analysis performed by sensor elements 6 and 7. One example of typical blood analysis is the measuring of the blood glucose level. Typically, 10 microliters are drawn for the blood test which requires the use of a glucose oxidase reagent layer. The glucose oxidase test is the standard test for blood glucose. Another typical analysis for a blood sample is the measurement of total blood protein. In this case, a copper tartrate reagent layer is used along with dry slide 8. This system may also be used for testing blood urine nitrogen content, along with any other typical component in blood under consideration.

Further, mounted within the portable housing is a laser energy source 11. The laser 11 is in optical communication with the disposable fluid displacement device 2. As shown in FIG. 6, the disposable fluid displacement device 2 includes an inner chamber 70 for drawing and receiving bodily fluid and two concentric outer chambers, an outer, annular chamber 56 for transmitting focused laser light onto the epidermis and an inner, annular chamber 58 for containing necessary power cables.

The laser energy source 11 transmits laser light through the disposable fluid displacement device 2, the laser light being focused onto the epidermis of a patient. The laser light is used to puncture the epidermis, creating a microscopic incision in the epidermal layer. The vacuum pump 9 then creates a drawn fluid path within the disposable fluid displacement device 2, allowing blood to be drawn up through the inner chamber 70 of fluid displacement device 2, the blood being received by removable dry slide 8. Sensor elements 6 and 7 are mounted within the hand-held housing on either side of the removable dry slide 8. Thus, sensor elements 6 and 7 may instantaneously analyze the blood sample collected on dry slide 8 at the site of the blood withdrawal.

As shown in FIGS. 1 and 2, laser energy unit 11, sensors 6 and 7, and power source 4 are all electrically coupled to logic processing unit 5. Power source 4 may be a set of standard rechargeable batteries or any other suitable portable electrical power source. Logic processing unit 5 controls the pulse rate of the laser energy source 11 and also performs the necessary analysis on the blood or other bodily fluid received by removable dry slide 8. Logic processing unit 5 may be composed of a clock coupled to a pulse modulator and include a pulse generator for providing pulsed energy from the energy source. The clock generates clock pulses at a rate at or above the highest frequency of the pumping pulses. Unit 5 may be programmed to provide standard analysis of the input data from sensors 6 and 7 dependent on a particular analysis desired.

Removable dry slide 8 may have a reagent layer formed thereon for interacting with the blood or other bodily fluids. Sensors 6 and 7, under the control of logic processing unit 5, determine the constituents of the blood or other bodily fluid by means of spectrographic, electrical, optical, or any other necessary analytical methodss. Logic processing unit 5 receives the output of sensors 6 and 7 and compares the measurements of sensors 6 and 7 with a set of known parameters regarding the bodily fluid under analysis.

Typically, in laser ablation systems, Er:YAG lasers are used for laser skin ablation. The Er:YAG lasers operate in the range of 2.94 micron wavelengths with an energy output of 160–180 mJ. Typically, in order to reduce pain and injury to the patient, the laser is pulsed with a pulse rate between 5 and 10 pulses per second. The pulse duration is typically on the order of 10 seconds.

Logic processing unit 5 may be reprogrammed by an outside source, such as a computer, through the power cables illustrated in FIG. 6. Thus, logic processing unit 5 may be used for the analysis and comparison of many different constituents for a variety of different bodily fluids.

Figure 3:
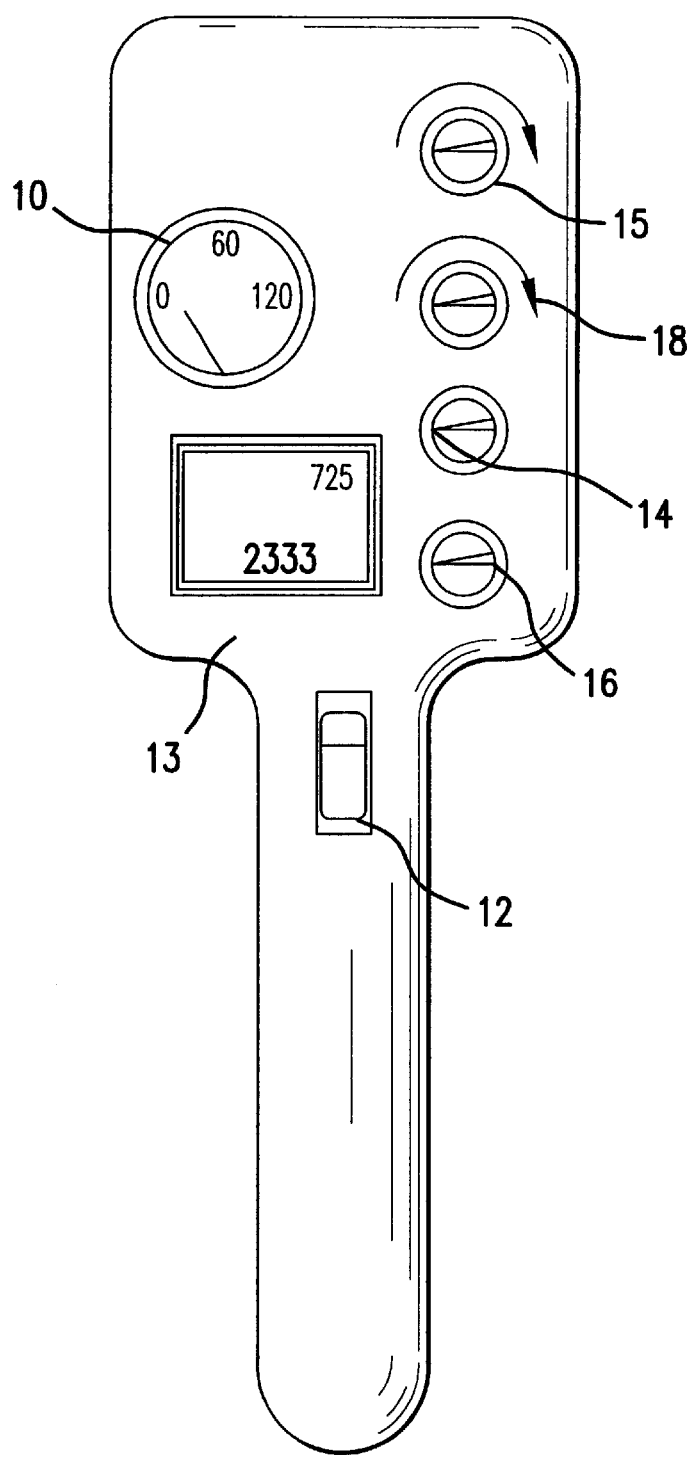
FIG. 3 is a top view of the subject non-invasive focused energy blood withdrawal and analysis system applicable to laser energy incision.

As shown in the top view of FIG. 3, system 1 includes a display unit 13. Display unit 13 may be an LED display, LCD display, or the like. Display 13 may be used to display the frequency and pulse rate of the laser energy source 11, the power level of the power source 4, or other necessary data for the operation of the non-invasive focused energy blood withdrawal and analysis system 1. Display unit 13 is electrically coupled to logic processing unit 5 and displays the results of the analysis, performed by sensor elements 6 and 7, of the drawn blood sample.

Additionally, as shown in FIG. 3, the system 1 includes a display gauge 10. Display gauge 10 is coupled to vacuum pump 9 and reads the associated power output, or relative fluid pressure, of the vacuum pump 9. Dial 16, shown in FIG. 3, is provided for variably controlling the power output of the vacuum pump 9. Dial 16 may be connected to a rheostat, variable resistor, or the like. Control over the strength of the vacuum is important in medical systems. High pressure differentials can lead to bruising and can be extremely painful for a patient. Thus, monitoring and control over the power output of vacuum pump 9 is necessary.

As further seen in FIG. 3, power switch 12 allows for manual actuation of the system 1 and is in electrical communication with the power source 4. Additionally, dial 14 allows for the manual control of the frequency of the pulsed laser 11. Similarly, dial 18 controls the power output of the laser energy source 11 and dial 15 controls the mode of the laser 11. Laser 11 may be used in a first cutting/ablation mode for creating the microscopic incision in the epidermal layer. Additionally, laser energy source 11 may be used in a thermal/coagulation mode. Using a low energy laser beam, the laser energy source 11 can be used for healing of the microscopic incision formed in the epidermis. The thermal/coagulation mode is also useful for sterilizing the incision.

Figure 4:
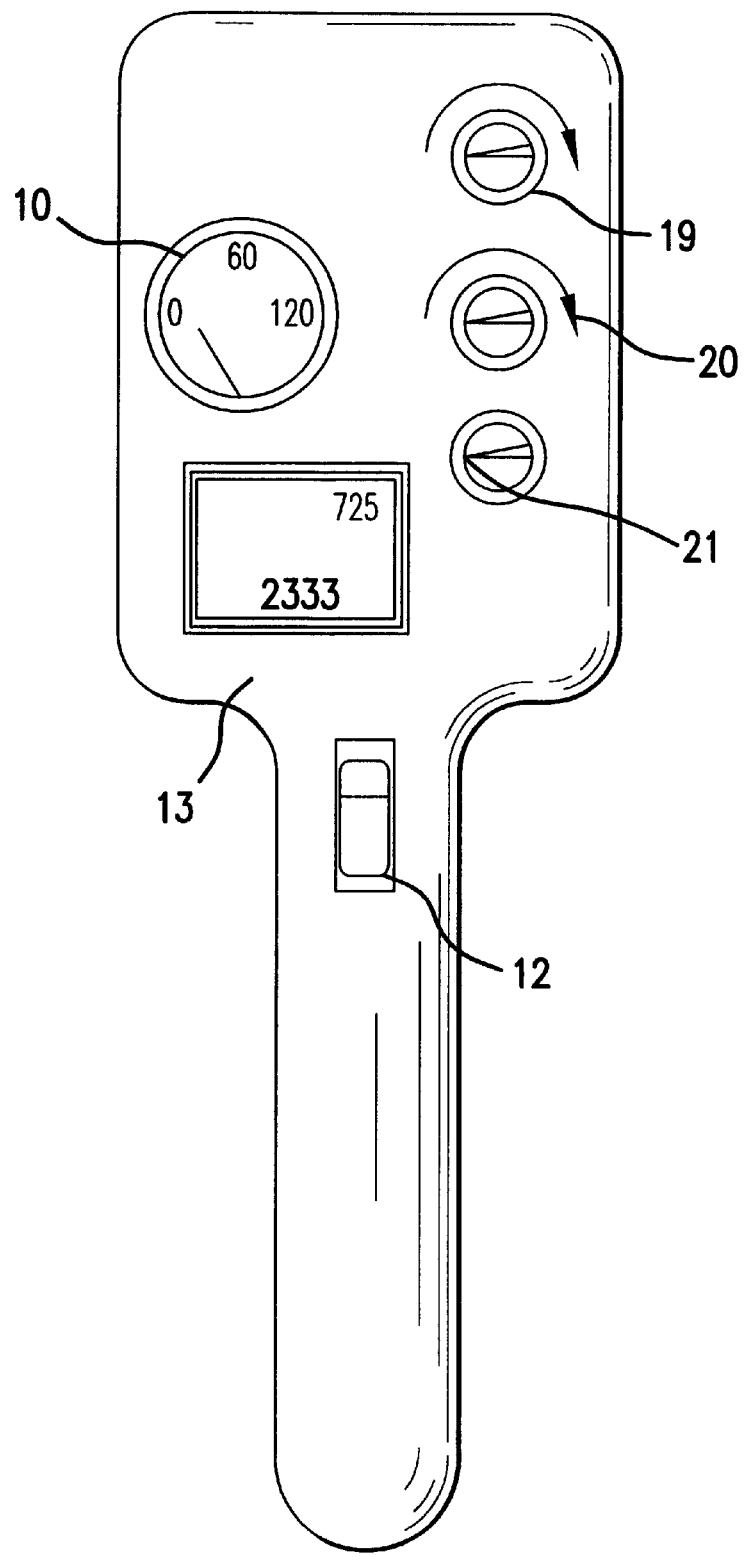
FIG. 4 is a top view of the subject non-invasive focused energy blood withdrawal and analysis system applicable to acoustic energy incision.
Figure 7:
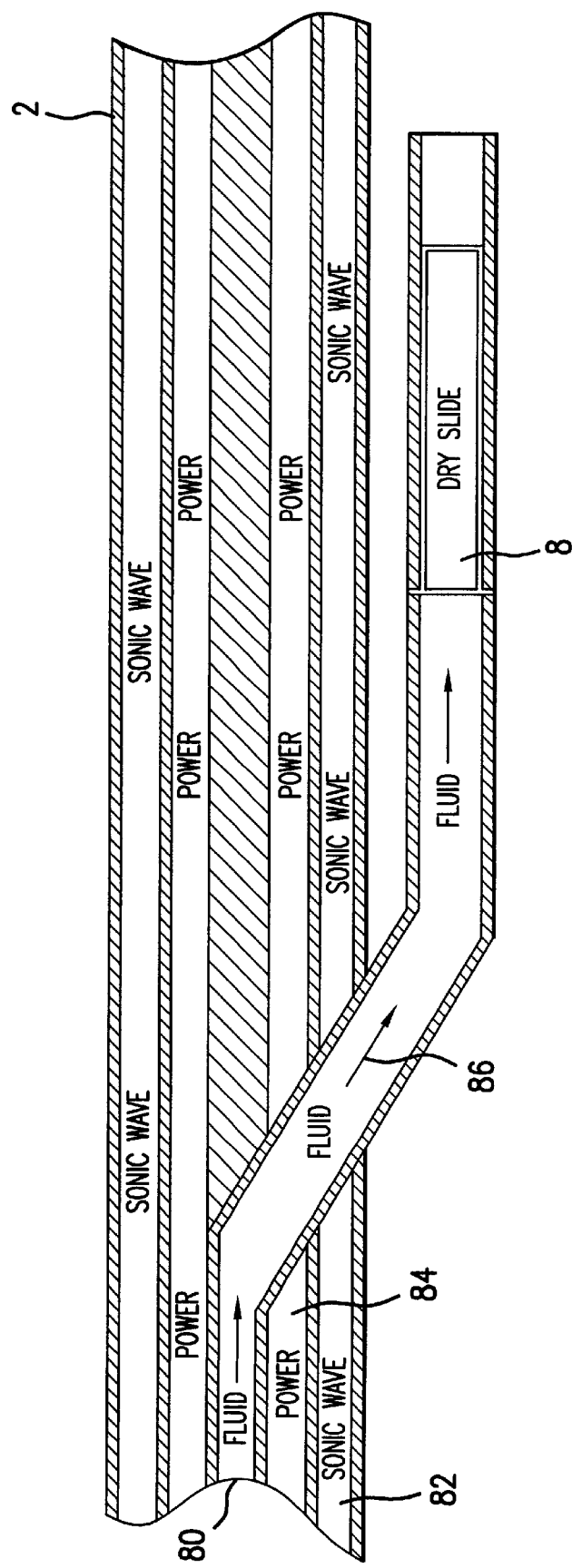
FIG. 7 is a partial cut-away side view of the acoustic non-invasive focused energy blood withdrawal and analysis system.

FIGS. 4 and 7 illustrate an alternative embodiment of the non-invasive focused energy blood withdrawal and analysis system. As shown in FIG. 7, sonic waves travel through the disposable fluid displacement device 2, rather than the focused laser beam of the previous embodiment. Here, acoustical energy is used to make a microscopic incision of the epidermal layer.

As shown in FIG. 7, the disposable fluid displacement tube 2 now includes an inner chamber 80 for withdrawing the bodily fluid to be analyzed, an outer annular chamber 82 through which the focused sonic wave is transmitted, and a tertiary annular chamber 84 through which the power cables are passed. After initiation of the sonic wave which travels through outer annular chamber 82, the fluid is withdrawn through the central chamber 80 along path 86 where it is received on dry slide 8.

Instead of a laser energy source 11, the present embodiment utilizes a sonic generator unit 11 to create sonic waves. The disposable fluid displacement device 2 transmits the focused sonic waves to the surface of the skin. Sonic generator 11 may be a piezoelectric generator or any other suitable generator of acoustical energy.

As shown in FIG. 4, dial 19 controls the cutting/ coagulation mode of the acoustical energy system. The frequency of the sonic waves is controlled by dial 20 and the power output of the vacuum pump 9 can be increased or decreased using dial 21. The display unit 13 and vacuum dial 10 are similar to those used in the laser energy embodiment.

In order to minimize damage to the patient's skin, the sonic energy source 11 has a power output of <1W. The frequency range may be between 2 kHz and 2 MHz.

Figure 5:
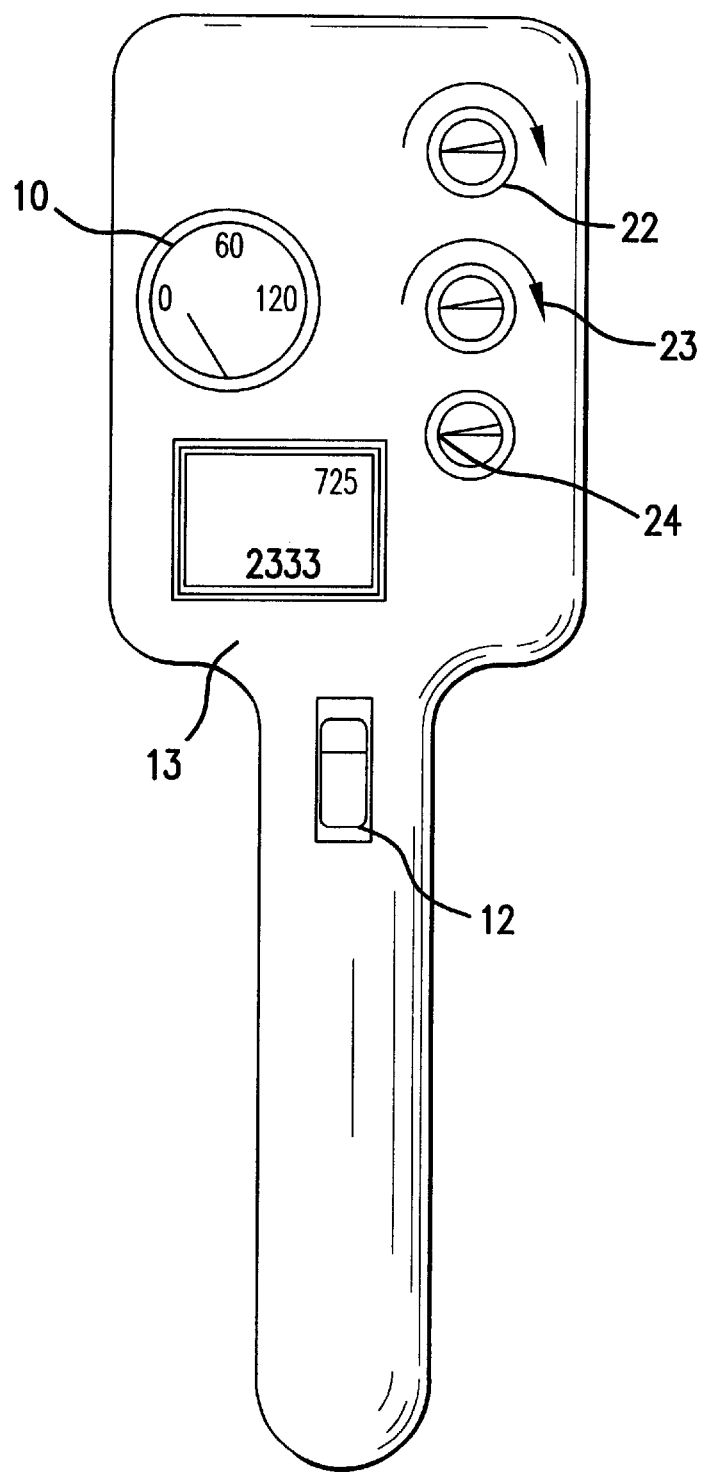
FIG. 5 is a top view of the subject non-invasive focused energy blood withdrawal and analysis system applicable to electrical current incision.
Figure 8:
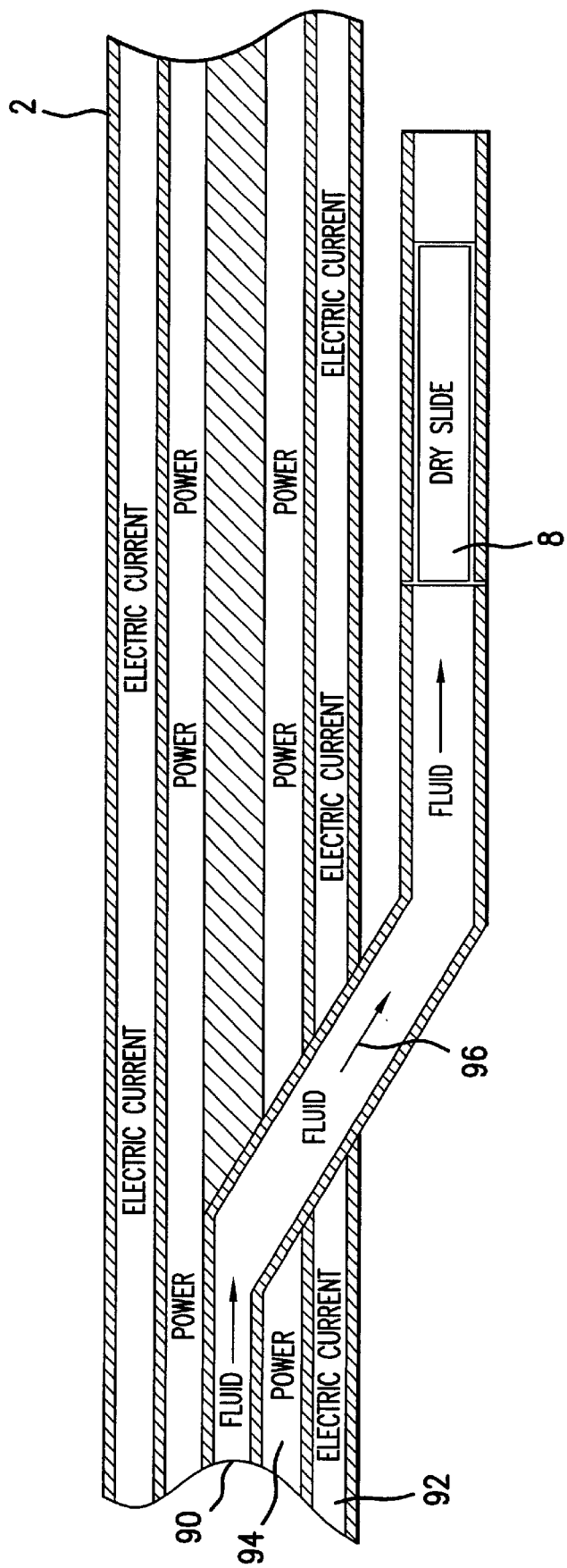
FIG. 8 is a partial cut-away view of the electrical current non-invasive focused energy blood withdrawal and analysis system; and, FIG. 9 is a flow block diagram of the focused energy blood withdrawal and analysis system for acoustic and laser energy systems.

FIGS. 5 and 8 illustrate another alternative embodiment of the non-invasive focused energy blood withdrawal and analysis system. As shown in FIG. 8, in this embodiment, the disposable fluid displacement device 2 has electrical cables in the place of the optic or acoustic energy of the previous embodiments. The electric cables are insulated along their length, down to the area of contact with the epidermal layer. These insulated electric cables are connected to logic 5 and power source 4.

As shown in FIG. 8, the disposable fluid displacement tube 2 includes a central chamber 90, an outer annular chamber 92, and an inner annular chamber 94. After actuation of the electrical current, which passes through electrical cables embedded within the outer annular chamber 92, the blood or other bodily fluid is drawn through central chamber 90 along fluid path 96 to be received on dry slide 8. Power cables are positioned within the inner annular chamber 94 for programming of the logic processing unit 5.

In this embodiment, electric current is used to create the microscopic incision in the epidermal layer. As shown in FIG. 5, the electric cutting mode is controlled using dial 22. Further, the electric coagulation mode is controlled using dial 23 and, similar to the previous embodiments, vacuum suction can be increased or decreased using dial 24. Display unit 13 and power switch 12 are similar to those in the optic and acoustic energy embodiments.

In order to minimize pain and injury to the patient's epidermal layer and the nerves in the dermal layer, the current must remain relatively low. Typical currents for skin ablation are in the range of 0.01 to 2 mA/cm$^2$.

In the laser energy system, in operation, the system power switch 12 is first switched on. The laser energy source 11 is then activated to ablate one, two, or more cells at a time in the epidermis. The power output of the laser 11 starts at a relatively safe level, such as 0.10 watts, and increases gradually.

In order to have a relatively painless procedure, the laser energy unit 11 is programmed at a pulse speed exceeding 5 pulses per second. The laser is also programmed to ablate one or more cells at a time. Minimal or no thermal energy is used in the ablation process.

Once the dermo/epidermal layer is reached, the cutting laser energy ruptures the arterioles, capillaries, and venules. Blood is typically under 25–33 mm of mercury pressure in the arterioles, capillaries, and venules. The blood follows a path toward areas of least resistance or lower pressure and, thusly, flows to the ablated area of the epidermis.

Vacuum suction created by vacuum pump 9 is then applied to the epidermal layer. The vacuum suction both accelerates the delivery of the blood sample needed for the analysis, and further ruptures the weak walls of the capillaries, thus adding more blood to the sample. The blood coming to the surface of the skin is withdrawn by the vacuum suction effect in the disposable fluid displacement device 2 and is received on removable dry slide 8.

Typically, 10 mL of blood is placed on removable dry slide 8. The dry slide 8 is composed of multiple specialized filter paper layers. The first one or two layers spread the molecules of blood evenly on the dry slide 8. The remaining layers contain reagents specific to the particular necessary blood test.

Sensor elements 6 and 7, in cooperation with processor 5, analyze the blood sample on the removable dry slide 8 and display the results on the display 13.

Once the test has concluded, a second laser pulse is sent to the microscopic hole formed in the epidermal layer. The laser energy is switched to a thermal or coagulation mode. The purpose of the thermal or coagulation laser pulse is to prevent bruising or further bleeding around the area of the microscopic hole.

The disposable unit 2, as well as the contacting, sealing member 3 and the removable dry slide 8 may then be discarded and replaced for use on the next patient.

The acoustic energy embodiment operates similarly to the optical energy system. The sonic wave generator generates waves of frequencies between 2 kHz and 2 MHz. In order to have a painless procedure, the sonic energy is programmed at a pulse rate exceeding 5 pulses per second.

The electrical energy system operates similarly to the laser and acoustic energy systems. Additionally, electrical energy may be used in combination with the laser energy or sonic energy systems to expedite the delivery of the blood sample and, more importantly, better control the ablation of the epidermis.

As there are nerve endings that may be stimulated by electrical current at the dermo/epidermal layer, it is safer to restrict the use of the electrical energy system to the superficial layers of the epidermis. Once the superficial layers of the epidermis have been ablated by the electrical energy, sonic energy or laser energy at a high pulse rate may be used to disrupt the walls of the small blood vessels at the dermo/epidermal layer.

Figure 9:
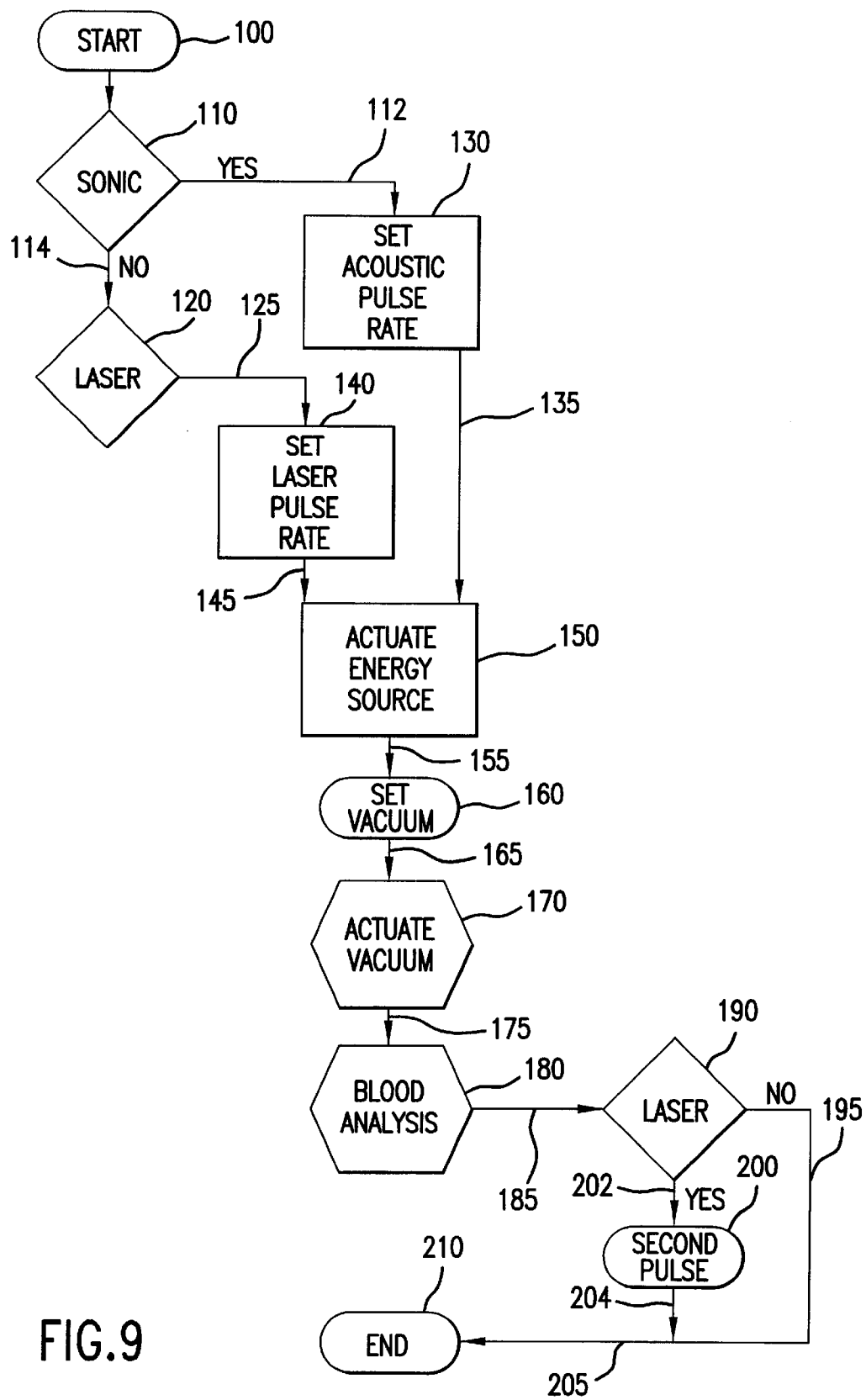

Logic processing unit or microprocessor 5 may be a standard IC chip such as the 82C85 (Harris) which is a low-power clock generator intended for the 80C/86/88 CMOS computing processor. The 82C85 chip has internal circuitry supporting stop-clock, stop-isolator, and low frequency operation. Referring now to FIG. 9, the logic flow begins at block 100 where the logic flows into decision block 110 to determine whether an acoustic actuation is to be initiated. In the event that an acoustic setting is provided, logic flows on line 112 to block 130 where the pulse rate for the acoustic generator is set.

If in the decision block 110 it is determined that it is not sonic or acoustic settings, logic flows on line 114 to decision block 120 where laser actuation is initiated and logic flows on line 125 to block 140 for setting the laser pulse rate as has been previously described.

Whether acoustic settings are dictated or laser settings have been dictated, logic flows respectively on lines 135 or 145 for actuation of the energy source in block 150.

Once the energy source has been actuated, logic on line 155 sets the vacuum back pressure in block 160 and the vacuum is actuated in block 170 through logic flow on line 165.

The data is passed to blood analysis block 180 on line 175 where the blood analysis is made in accordance with standard procedures as previously described. Once the blood analysis has been completed, logic on line 185 is led to decision block 190 to determine whether a laser setting has been dictated. In the event that the laser setting has been dictated, logic flows on line 202 to block 200 where a second laser pulse is provided. The logic then flows on line 204 and 205 to block 210 where the procedure is ended. In the event that the acoustic or sonic actuation has been dictated, the logic flows on line 195 and 205 to the termination block 210.

Although this invention has been described in connection with specific forms and embodiments thereof, it will be appreciated that various modifications other than those discussed above may be resorted to without departing from the spirit or scope of the invention. For example, functionally equivalent elements may be substituted for those specifically shown and described without departing from the spirit or scope of the invention as defined in the appended Claims.

What is claimed is:

1. A non-invasive focused energy blood withdrawal and analysis system comprising:

a housing;

an energy source mounted within said housing for generating an energy beam, said energy beam being focused on an epidermal layer to create a microscopic opening in said epidermal layer;

a logic processing unit electrically coupled with said energy source for controlling said energy source;

a vacuum pump mounted within said housing;

a suction tube having a first end in fluid communication with said vacuum pump and a second end placed over said microscopic opening to draw a blood sample in a fluid path within said suction tube;

a slide located in said fluid path of said blood sample and removably mounted within said housing for collecting said blood sample; and, at least one sensor in electrical communication with said logic processing unit for analyzing said blood sample collected on said slide.

2. The non-invasive focused energy blood withdrawal system as recited in claim 1 wherein said energy source is a laser.

3. The non-invasive focused energy blood withdrawal system as recited in claim 1 wherein said energy source is a sonic wave generator.

4. The non-invasive focused energy blood withdrawal system as recited in claim 1 wherein said energy source is an electrical power source.

5. The non-invasive focused energy blood withdrawal system as recited in claim 1 wherein said slide has a reagent layer formed thereon.

6. The non-invasive focused energy blood withdrawal system as recited in claim 1 wherein said vacuum pump has a variable power output.

7. The non-invasive focused energy blood withdrawal system as recited in claim 1 wherein said energy beam is pulsed at a controllable pulse rate.

8. The non-invasive focused energy blood withdrawal system as recited in claim 1 wherein said housing has a display mounted thereon, said display being in electrical communication with said logic processing unit.

9. The non-invasive focused energy blood withdrawal system as recited in claim 1 wherein said energy source has a variable power output.

10. The non-invasive focused energy blood withdrawal system as recited in claim 1 wherein said energy beam has a variable frequency.

11. A non-invasive focused energy blood withdrawal and analysis system comprising:

a hand-held housing;

an energy source mounted within said housing for generating an energy beam, said energy beam being focused on an epidermal layer to create a microscopic opening in said epidermal layer;

a logic processing unit electrically coupled with said energy source for controlling said energy source;

a vacuum pump mounted within said housing;

a suction tube removably mounted within said hand-held housing, said suction tube having a first end in fluid communication with said vacuum pump and a second end placed over said microscopic opening to draw a blood sample in a fluid path within said suction tube;

a slide located in said fluid path of said blood sample and removably mounted within said housing for collecting said blood sample;

a sealing member removably fixed to the base of said hand-held housing for contacting said epidermal layer; and, at least one sensor in electrical communication with said logic processing unit for analyzing said blood sample collected on said slide.

12. The non-invasive focused energy blood withdrawal system as recited in claim 11 wherein said energy source is a laser.

13. The non-invasive focused energy blood withdrawal system as recited in claim 11 wherein said energy source is a sonic wave generator.

14. The non-invasive focused energy blood withdrawal system as recited in claim 11 wherein said energy source is an electrical power source.

15. The non-invasive focused energy blood withdrawal system as recited in claim 11 wherein said slide has a reagent layer formed thereon.

16. The non-invasive focused energy blood withdrawal system as recited in claim 11 wherein said vacuum pump has a variable power output.

17. The non-invasive focused energy blood withdrawal system as recited in claim 11 wherein said energy beam is pulsed at a controllable pulse rate.

18. The non-invasive focused energy blood withdrawal system as recited in claim 11 wherein said hand-held housing has a display mounted thereon, said display being in electrical communication with said logic processing unit.

19. The non-invasive focused energy blood withdrawal system as recited in claim 11 wherein said energy source has a variable power output.

20. The non-invasive focused energy blood withdrawal system as recited in claim 11 wherein said energy beam has a variable frequency.

* * * * *